United States Patent [19]
Krieger

[11] Patent Number: 5,830,183
[45] Date of Patent: Nov. 3, 1998

[54] CLIP DEVICE FOR VASCULAR CATHETER

[75] Inventor: Sarah J. Krieger, Victoria, Minn.

[73] Assignee: Schneider (USA) Inc, Minneapolis, Minn.

[21] Appl. No.: 885,533

[22] Filed: Jun. 30, 1997

[51] Int. Cl.[6] .................................................. A61M 29/00
[52] U.S. Cl. ............................. 604/96; 606/194; 24/16 R; 24/327
[58] Field of Search ............................. 604/96–102, 283, 604/280, 264; 606/192, 194; 24/273, 16 R, 16 PB, 327, 489, 570

[56] References Cited

U.S. PATENT DOCUMENTS

| | | |
|---|---|---|
| Re. 33,166 | 2/1990 | Samson . |
| Re. 34,564 | 3/1994 | Mar et al. . |
| Re. 35,176 | 3/1996 | Powell . |
| 2,845,930 | 8/1958 | Brown ........................................ 604/96 |
| 3,429,985 | 2/1969 | Czigler ..................................... 24/16 R |
| 3,670,369 | 6/1972 | McIlory, II ........................... 24/16 PB |
| 4,323,071 | 4/1982 | Simpson et al. . |
| 4,411,055 | 10/1983 | Simpson et al. . |
| 4,571,240 | 2/1986 | Samson et al. . |
| 4,573,470 | 3/1986 | Samson et al. . |
| 4,582,181 | 4/1986 | Samson . |
| 4,597,755 | 7/1986 | Samson et al. . |
| 4,619,263 | 10/1986 | Frisbie et al. . |
| 4,638,805 | 1/1987 | Powell . |
| 4,641,654 | 2/1987 | Samson et al. . |
| 4,664,113 | 5/1987 | Frisbie et al. . |
| 4,692,200 | 9/1987 | Powell . |
| 4,730,616 | 3/1988 | Frisbie et al. . |
| 4,771,776 | 9/1988 | Powell et al. . |
| 4,771,778 | 9/1988 | Mar . |
| 4,775,371 | 10/1988 | Mueller, Jr. . |
| 4,782,834 | 11/1988 | Maguire et al. . |
| 4,790,315 | 12/1988 | Mueller, Jr. et al. . |
| 4,793,350 | 12/1988 | Mar et al. . |
| 4,838,269 | 6/1989 | Robinson et al. . |
| 4,928,693 | 5/1990 | Goodin et al. . |
| 4,976,720 | 12/1990 | Machold et al. . |
| 5,093,964 | 3/1992 | Rowland ................................. 24/16 R |
| 5,098,379 | 3/1992 | Conway et al. ......................... 604/51 |
| 5,295,961 | 3/1994 | Niederhauser et al. . |
| 5,354,282 | 10/1994 | Bierman . |
| 5,364,355 | 11/1994 | Alden et al. .............................. 604/96 |
| 5,372,592 | 12/1994 | Gambale ................................. 604/165 |
| 5,460,185 | 10/1995 | Johnson et al. . |
| 5,489,271 | 2/1996 | Andersen . |
| 5,496,346 | 3/1996 | Horzewski et al. . |
| 5,702,364 | 12/1997 | Euteneuer et al. ........................ 604/96 |

Primary Examiner—Wynn Wood Coggins
Assistant Examiner—Deborah Blyveis
Attorney, Agent, or Firm—Haugen and Nikolai, P.A.

[57] ABSTRACT

A vascular dilatation catheter including an elongated catheter shaft having a distal and a proximal end and a first lumen extending therethrough fluid connection with a distally located balloon and a second lumen capable of receiving a guidewire is provided with a clip device attached about a proximal portion of the catheter shaft and adapted to releasibly secure the catheter shaft in a coiled configuration between uses.

14 Claims, 6 Drawing Sheets

CLIP DEVICE FOR VASCULAR CATHETER

BACKGROUND OF THE INVENTION

I. Field of the Invention

The present invention relates generally to vascular catheter systems and particularly to catheter systems that employ inflatable balloon devices to accomplish mechanical dilitation of vascular stenoses, more particularly those occurring in coronary arteries. The invention itself involves a clip device for convenient temporary retention of a catheter shaft in coiled form during interim periods when one of possibly several catheters being used in a procedure is temporarily removed from a guidewire between uses during the procedure. The clip device is preferably a single piece and includes a hub.

II. Related Art

Percutaneous dilitation of coronary stenoses by balloon dilitation catheter devices has evolved into an accepted or standard approach to alleviating many types of arterial blockages, especially partial coronary blockages, as it has, over the years, been demonstrated to be an effective, relatively low-risk procedure. During such procedures, often several different types of dilitation catheters are employed sequentially utilizing the same guidewire and, in some cases, the catheters may be alternately used several times, being inserted through the vascular system over an already indwelling guidewire. The catheter shafts are typically quite long, i.e., from about 70 cm. to about 150 cm. Once removed from the guidewire, the entire catheter may be set aside and kept within the sterile field for reuse. The length of the catheter shaft makes this quite inconvenient and awkward. No convenient device has been available to retain the catheter shaft in the coiled configuration until the next use. Thus, there remains a need for a system, particularly one integral with the catheter device itself for the temporary storage of the catheter shaft between uses which is easily operable and does not in any way interfere with the designed use of the catheter system.

Accordingly, it is a primary object of the present invention to provide an retention system for retaining a vascular catheter shaft in a relatively compact coiled configuration between the uses thereof.

Another object of the present invention is to provide a retention system for a coiled catheter shaft which is an integral part of and does not otherwise interfere with the normal operation of the catheter.

Yet another object of the present invention is to provide an integral hub/clip retention system for a coiled catheter shaft that is inexpensive and easy to operate.

Other objects and advantages of the invention will become apparent to those skilled in the art upon familiarization with the specifications, drawings and claims contained in this application.

SUMMARY OF THE INVENTION

According to the present invention, there is provided a convenient, easy to operate combination hub and clip device for releasibly securing an associated catheter shaft in a coiled configuration between deployments thereof. According to the invention, a hollow clip device is mounted at the proximal end of the catheter shaft and is designed to connect the catheter shaft to any associated external devices such as combined guidewire and inflation fluid input manifolds, or the like. The clip is designed with a hollow interior which allows the manifold or other connected device to access the various catheter lumens as desired. The clip device may incorporate a hub which, in turn, may be provided with an integral leuer proximal fitting to engage the manifold or other such connectable device. Of course, any other desired fitting may be molded to the body of the clip, without limitation.

The clip device particularly includes a system for releasibly securing the catheter shaft in a coiled configuration of one or more loops. This includes the provision of an external recess for accommodating a plurality of loops of the catheter shaft in the coiled configuration and a hinged clasp lid for providing a reclosable snap-fit latch over the coiled shaft to retain the coiled catheter shaft in the recess. The hinge attaching the clasp lid to the body of the clip is a flexible but preferably integral part of the clip device.

The clip including the hinged clasp lid is preferably molded as a single-piece system with the hinge being a "living" hinge capable of easy flexure and capable of being flexed a plurality of times during which the clasp lid is repeatedly opened and closed. The clip and clasp lid may be molded from a single polymer material in a one-shot injection molding operation. It is further contemplated, however, that a plurality of materials could be used, including a material for the hinge and clip that is somewhat softer and more pliable than that utilized for the main body of an associated hub. It should be recognized further that any appropriate moldable plastic material can be used for the device that is capable of being formed with internal passages and retaining its shape during use. These include many acrylic and polycarbonate materials, styrenes, ABS and other materials. The hinge and clip may be made of the same or rather softer polyester materials such as polyesters including Hytrel (Dupont), nylons, and other polymer materials such as polyethylenes, polypropylenes and other compatible materials. If two different materials are used, the device can be made by a two-shot process whereby both materials are injected at different gates into the mold cavity. Other processes are also feasible, such as insert molding.

An aspect of the integral hub and clip system of the invention is the harmonious manner in which the device can be incorporated in the catheter system without affecting the catheter itself or the devices to be attached to the proximal end of the catheter. In addition, it utilizes an easily operable snap lid latch and the overall configuration is one which does not interfere with the normal use and operation of the catheter system or get in the way during its use in a procedure.

BRIEF DESCRIPTION OF THE DRAWINGS

In the drawings, wherein like parts are represented by like reference numerals throughout the same.

DETAILED DESCRIPTION

In the detailed description, the combination hub clip is illustrated with regard to one or more particular embodiments. These embodiments are intended merely to illustrate the principles of the invention and not to limit the outward appearance or possible uses of the system. It is contemplated, for example, that the hub may be mounted on different catheter devices.

Figure 1:
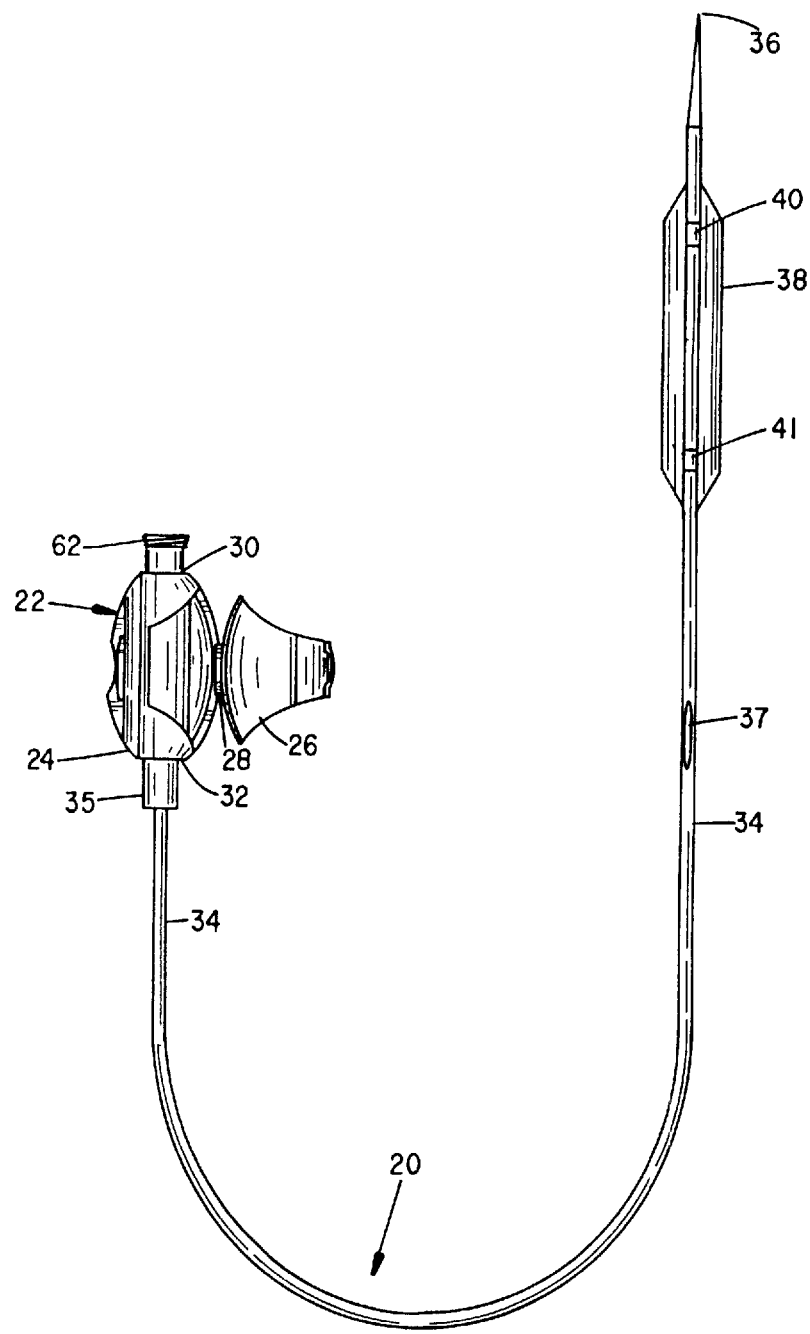
FIG. 1 depicts a rapid exchange balloon dilitation catheter including the clip device of the invention.

FIG. 1 illustrates a rapid exchange balloon dilitation catheter device of a class suitable for and, in fact, incorporating the hub clip system of the invention. The catheter device is generally represented by the number 20.

The connecting hub is depicted at 22, including a body element 24 and a clasp lid 26 suitably and integrally hinged at 28 to the body element 24. The proximal end 30 of the hub device 22 may be connected removably to any suitable accessory such as a manifold in the form of an integral Y-adaptor (FIG. 2) as by a leuer fitting, 62 or the like. The distal end 32 is adapted to receive the catheter shaft 34 utilizing a reinforcing or strengthening transition segment 35. A shive or guidewire port for the rapid exchange catheter device is shown at 37. A dilitation balloon or expander device 38 incorporated as part of the catheter 20 in a well-known manner. Radiopaque markers useful for assisting placement and positioning of the expander 38 are depicted by 40 and 41.

Figure 2:
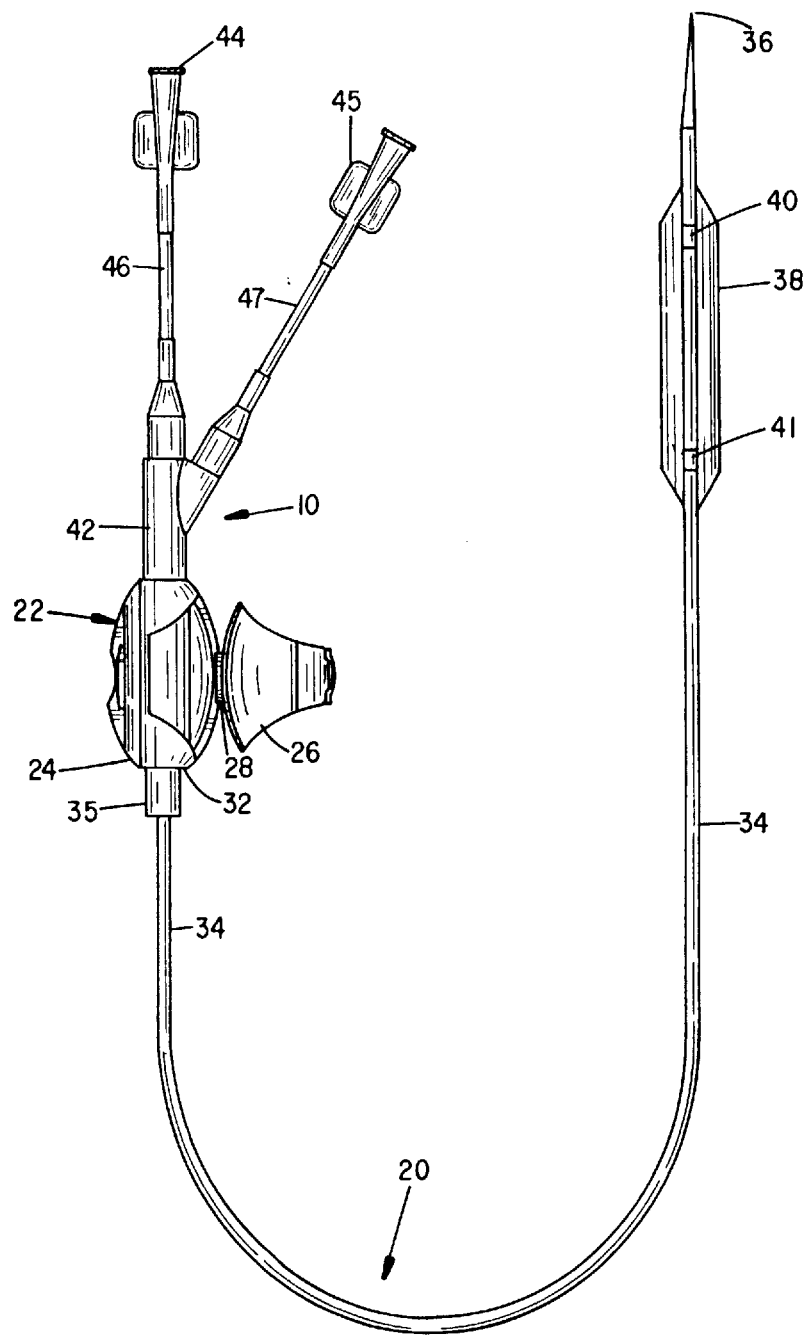
FIG. 2 depicts an over the wire balloon dilitation catheter including the clip device of the invention.

FIG. 2 illustrates the over the wire dilitation catheter device of FIG. 1 incorporating the clip system of the invention in which the proximal end of the hub device includes an integral Y-adaptor shown generally as 42. The adaptor 42 connects and accesses external devices using tubular ports, examples of which are depicted at 44 and 45 with connecting members 46 and 47, respectively. Separation between access via Y-adaptor 42 is maintained internally in a well-known manner.

The illustrated catheter shaft 34 of FIG. 2 is typically a two-lumen shaft that includes a guidewire lumen through which a guidewire, the tip of which appears at 36, can be threaded using one of the accesses 44 and 45. Of course, any rethreading of a catheter for a second or third use involves threading the catheter over a guidewire already in place in the vascular system. The other access 44 or 45 is connected with a pressure lumen which serves to conduct fluid reversibly from a source to inflate the dilitation balloon or expander device 38.

Figure 3:
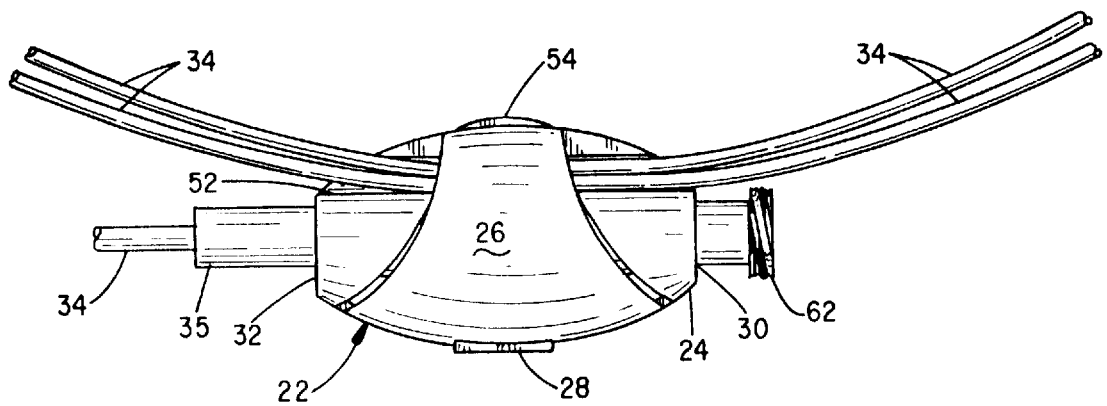
FIG. 3 is an enlarged view of the clip of FIG. 1 with the clasp lid latched in the closed position and illustrating several loops of a coil of the catheter shaft shown broken and secured to the hub by the closed clasp lid.
Figure 4:
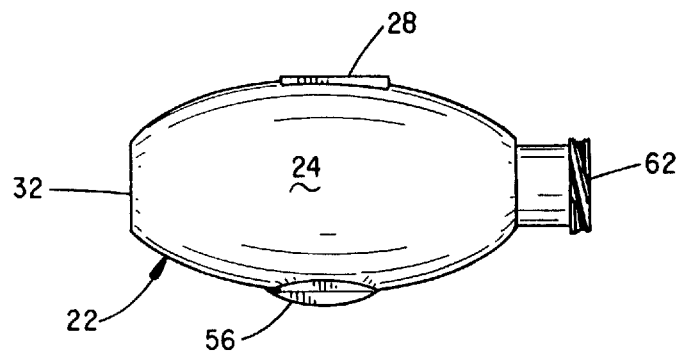
FIG. 4 is a bottom view of the hub of FIG. 3 without the illustrated coils.
Figure 5:
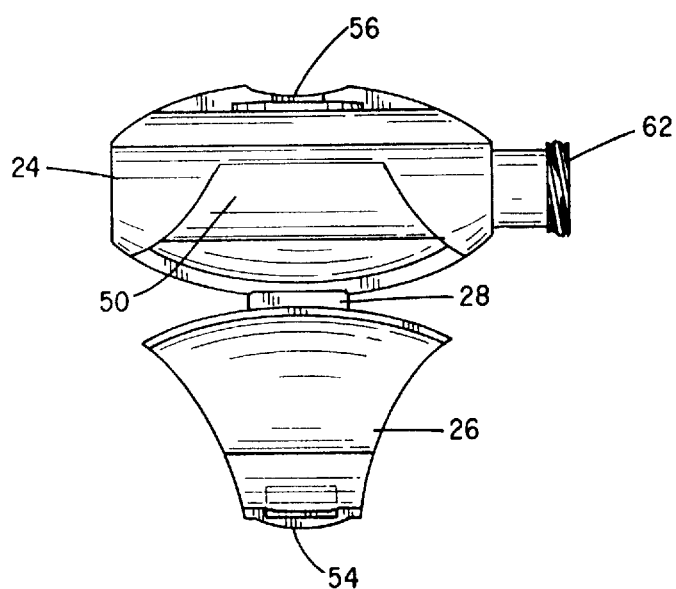
FIGS. 5 and 6 illustrate views of the hub device of FIGS. 3 and 4 with the clasp lid open.
Figure 6:
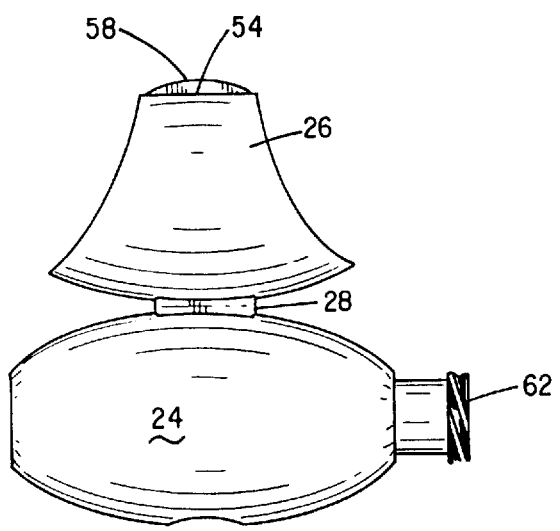
Figure 7:
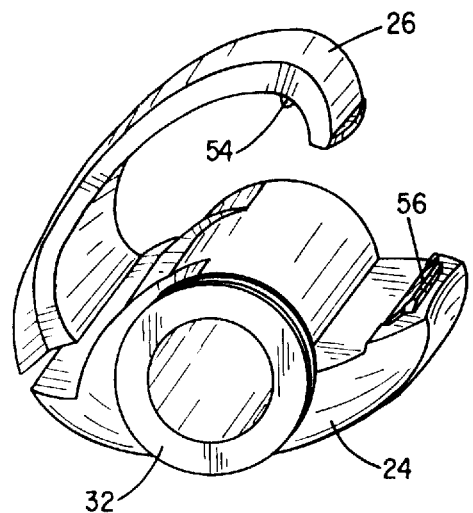
FIGS. 7 and 8 are enlarged perspective views of a hub device with the clasp lid in the open and closed positions, respectively, showing a possible latch.
Figure 8:
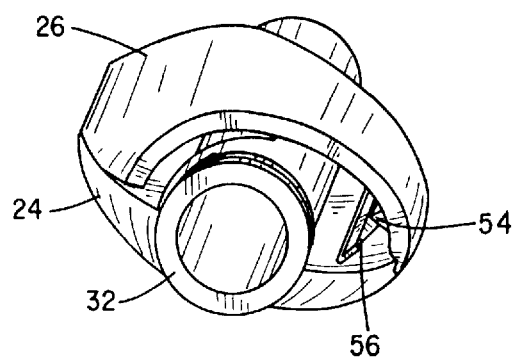

The clip device itself is depicted in greater detail in FIGS. 3–8. As can be seen from the figures, the body 24 of the hub device 22 is provided with a shallow recess at 50 (FIG. 5) to accommodate a portion of the clasp lid 26 thereby maintaining relatively smooth outer configuration for the hub when the clasp lid is closed. The hub device is further provided with a longitudinal open-ended recess 52 which is designed to accommodate and capture one or more turns or coils of the catheter shaft 34 as shown in FIG. 3. A snap-fitting clasp or catch lip is illustrated on the lid at 54 which cooperates with a catch 56 on the clip body to provide a finger-operable snap-fit closure. These features are shown exaggerated in FIGS. 7 and 8 for the purposes of illustration only.

The configuration and operation of snap latches of the class is quite well known and it will be appreciated that the force required to open and close such a latch can be varied with respect to the construction of the device such that the desired closure tension is achieved. It will be appreciated that the hinge member 28 is preferably rather thin and able to accommodate a number of repeated flexings while functioning so that it remains intact in a manner such that the clasp lid 26 may be operated a number of times to capture and release turns of the catheter shaft as necessary during the use of the catheter in a procedure. It will further be noted that the system can readily be operated occupying but one hand of the user.

The device itself is preferably molded in a one or two-shot molding operation with the hinge and lid portion being integrally formed. The entire assembly may be constructed of a single molded polymeric material in a one-shot process or may utilize diverse materials for the main body of the hub and the hinge and clip. In this manner, the system may be formed using a multi-step process with a plurality of materials possibly in a two-shot process in which both materials are injected at separate accesses into the mold cavity. Of course, other established processes of fabricating such devices, such as insert molding, may be employed by those skilled in the art as well.

It will be appreciated that any moldable polymer material susceptible of forming the hub with the required internal passages and external recess, together with the integral living hinge and clasp lid and which is compatible with the remainder of the catheter device may be utilized. The list of materials includes, but clearly is not limited to, acrylic materials, polyester materials, polycarbonate materials, styrene, ABS and many others. A slightly softer material such as Hytrel polyester and various polyalkene materials such as polyethylene and polypropylene may be utilized for the hinge and clip portion, assuming that a harder material is used for the associated hub itself, if desired.

The clip device of the present invention may form the proximal end of a catheter. Alternatively, it may be attached to a catheter shaft at a point distal of the proximal end of the catheter, such as within 10 cm. of the proximal end of the catheter in which case the catheter shaft would pass through and be bonded to an inner lumen of the clip.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A vascular dilatation device comprising:
   (a) a dilatation balloon catheter including an elongated catheter shaft having a distal end and a proximal end, said catheter shaft having a first lumen extending therethrough and in fluid connection with a distally located balloon and a second lumen capable of receiving a guidewire;
   (b) a hub device for connecting the catheter to external devices attached to the proximal end of said catheter shaft; and
   (c) a hinged clip device for releasibly securing at least one loop of said catheter shaft to said hub in a coiled disposition, the clip device being integral with said hub and formed as a single piece with said hub including a hub body, a clip lid for providing a reclosable retainer to releasibly secure said at least one loop of said catheter shaft, and a living hinge joining the clip lid to the hub body.

2. The device of claim 1 wherein said clip lid further forms an external recess with said hub body for accommodating said at least one loop of said catheter shaft in a coiled configuration which cooperates with said clip lid providing a reclosable snap-fit system to releasibly secure said coiled catheter shaft in said recess.

3. The device of claim 2 wherein the hub body and clip lid are molded from a single polymer material.

4. The device of claim 3 wherein said hub body is made from material selected from the group consisting of polyesters and polycarbonates.

5. The device of claim 2 wherein the hub and said clip lid are molded using two different polymer materials.

6. The device of claim 2 wherein said living hinge and said clip lid are made from a softer material than the hub body.

7. The device of claim 2 wherein the proximal end of the clip device includes a male leuer connection.

8. The device of claim 1 wherein said clip device provides a smooth continuation of the surface of the hub when said clip lid is closed.

9. The device of claim 8 wherein said hub body is made from material selected from the group consisting of polyesters and polycarbonates.

10. The device of claim 1 wherein the clip lid has a finger operable snap-fit closure.

11. The device of claim 1 wherein the hub body and clip lid are molded from a single polymer material.

12. The device of claim 1 wherein said hub and said clip lid are molded using two different polymer materials.

13. The device of claim 1 wherein said living hinge and said clip lid are made from a softer material than said hub body.

14. The device of claim 1 wherein the proximal end of the clip device includes a male luer connection.

* * * * *